United States Patent [19]

Tsuda et al.

[11] 4,207,188
[45] Jun. 10, 1980

[54] OPEN TUBULAR CAPILLARY COLUMN FOR HIGH-SPEED MICRO LIQUID CHROMATOGRAPHY

[75] Inventors: Takao Tsuda, Aichi; Kiyokatsu Hibi, Ohgaki; Toyohide Takeuchi, Tokoname; Tomohiko Nakanishi, Kariya; Daido Ishii, Nagoya; Koichi Mochizuki, Tsushima, all of Japan

[73] Assignee: Japan Spectroscopic Co. Ltd., Tokyo, Japan

[21] Appl. No.: 938,350

[22] Filed: Aug. 31, 1978

[30] Foreign Application Priority Data

Dec. 24, 1977 [JP] Japan ................................ 52-156123

[51] Int. Cl.$^2$ ............................................. B01D 15/08
[52] U.S. Cl. .................................... 210/198 C; 55/386
[58] Field of Search ............. 210/31 C, 198 C; 55/67, 55/386; 427/333, 407 A, 230-233, 235, 238

[56] References Cited

U.S. PATENT DOCUMENTS

| 3,666,530 | 5/1972 | Aue et al. | 210/198 C |
| 4,043,905 | 8/1977 | Novotny | 210/198 C |
| 4,054,432 | 10/1977 | Taylor | 55/386 |
| 4,059,523 | 11/1977 | Mochizuki et al. | 210/198 C |

OTHER PUBLICATIONS

"Laboratory-Made Porous Layer Gas Chromatography Columns", by Nikelly and Blumer American Laboratory, Jan. 1974, vol. 6 No. 1, pp. 12, 13, 14, 16.

*Primary Examiner*—John Adee
*Attorney, Agent, or Firm*—Browdy and Neimark

[57] ABSTRACT

An open tubular capillary column, for high-speed micro liquid chromatography made of a glass tube of the inner diameter not more than 0.10 mm, having the net inside capacity not less than 0.5 $\mu$l, the inner surface of which hollow glass tube being chemically bonded, in order to provide a stationary phase there, with at least one silane or its derivative such as octadecylsilane to form a polymeric layer. This invention includes the manufacturing method of such a column.

6 Claims, 4 Drawing Figures

OPEN TUBULAR CAPILLARY COLUMN FOR HIGH-SPEED MICRO LIQUID CHROMATOGRAPHY

BACKGROUND OF THE INVENTION

The present invention relates to an open tubular capillary column preferably usable for high-speed micro liquid chromatography and the manufacturing method therefor, more particularly, to the provision of an open tubular capillary column capable of high sensitive detection and microanalysis, having a stable stationary phase.

In recent years, liquid chromatography has made a rapid progress along with, or with the aid of, the development of high-pressure pumps or the enhancement of separating capability of column packing materials. As a high-speed system, wherein a mobile phase is flowed in high-speed for rapid separation, liquid chromatography has been recognized to be a highly effective separating and analytical technique in the field of chemistry, biology, medical science, etc.

Columns used for such a high-speed liquid chromatography are required, from the standpoint of increasing of the separating speed, high capability of microanalysis, high degree separating capability, economy of column packing materials or media, etc., to be as small as possible in the inner diameter thereof. In the actual practice, columns of 2.5 mm, more or less, are widely used. Further diminishing of the inner diameter down to 1.0 mm to 0.5 mm has been conventionally deemed very difficult or impracticable, because small recesses, jogs, or roughness on the inner wall surface of the column may directly affect the separating capability.

A column of the inner diameter approximately 0.5 mm and the relevant technology has been disclosed in the Japanese Patent Application TOKU-GAN-SHO-49 (1974)-72107 as well as in the U.S. Pat. No. 4,059,523. This column may be used in a high-speed liquid chromatography at the flow rate of 10 $\mu$/min. more or less. Even such a small diametered column of glass tube, however, is not free from using a column packing material; and packing a column packing material to the column with such a small diameter is not an easy job.

In the gas chromatography, on the other hand, a so-called Golay column, a kind of open tubular capillary column in which no column packing is used but a liquid phase (stationary phase) is instead held, is known. This Golay column enables one to eliminate the troublesome packing operation of the column packing material. It is quite natural therefore that this art led the researchers in the field to the application of an open tubular capillary column of this type even to liquid chromatography. No successful cases, however, have been reported so far. This may be attributable to a fundamental difference of the mobile phase between gas chromatography and liquid chromatography. Before applying the art in gas chromatography to that in liquid chromatography, difference in the capillary column design due to the difference of the diffusion coefficient should be solved first. This is the very problem that motivated this invention. This is the very reason that the technology in gas chromatography can not be applied as it is to liquid chromatography.

We thought the essential problem for obtaining an ideal column for liquid chromatography is to determine the design conditions for relatively diminishing the diffusion of the sample in the mobile phase liquid. We found, after a series of experiments, that the inner diameter of the column of glass tube should be 0.10 mm or less and the length thereof should be determined as to make the net inside capacity 0.5 $\mu$l or more, preferably 1.0 $\mu$l or more. A column satisfying such conditions have been found to be of very high separating capacity at a high theoretical plate number. Another problem must be solved before practically applying such a column to the liquid chromatography, i.e., the problem of coating a stationary phase on the inner surface of the column of glass tube, which is a prerequisite condition therefor. A proper measure must be taken for preventing solution of the stationary phase into the mobile phase, as well as the accompanying exfoliation or mechanical scaling-off of the stationary phase, because the stationary phase is soluble into the mobile phase, although slightly, and the mobile phase runs fast when a high-speed separation is executed. Further research for preventing the mechanical scaling-off of the mobile phase in such a small diametered thin column has led us to the under-mentioned discovery. Noticing that glass, which constitutes a principal material of the column, has on its surface silanol groups, we thought of chemically bonding this kind silanol group with a silane or its derivative, which is to become a stationary phase, for forming a stable layer of silane or its derivative chemically bonded on the inner surface of the column of glass. It has been found that a layer of silane or any derivative thereof is very useful as a stationary phase. This invention has thus been completed on such a basic idea.

SUMMARY OF THE INVENTION

A principal object of this invention is therefore to provide an open tubular capillary column preferably usable for high-speed micro liquid chromatography.

Another object of this invention is to provide an open tubular capillary column, being capable of high sensitive detection and microanalysis, and having a stable stationary phase.

A further object of this invention is to provide a manufacturing method of a practical open tubular capillary column of high separating capability in microanalysis, high-speed separation, and high theoretical plate number.

Other objects and advantages of this invention will be apparent from the studying of the under-mentioned detailed description of the embodiments and accompanying drawings.

For achieving those objects, this invention employs an open capillary column of glass tube having the inner diameter not more than 0.10 mm and the net inside capacity not less than 0.5 $\mu$l, and providing, on the inner surface thereof, a stationary phase of polymeric layer, which is formed by a chemical bonding of at least one silane or its derivative with the inner surface of the column. Practically a column of glass tube is first cleaned or rinsed on its inner surface, and then the silane or its derivative is applied or coated on the inner surface of the same, before conducting a heat treatment, for chemically bonding both.

In this way, an open capillary column has been practically introduced for the first time in the field of liquid chromatography by virtue of this invention. A column of this kind of high performance for microanalysis, high-speed separation, and separation in the high theoretical plate number is therefore easily manufactured. As this open capillary column does not, as in the prior art, use stationary phase carrier (packing material) at all, the troubles of packing or other problems derived from the packing materials have been completely eliminated. Characteristics of chemical bonding of the silane or its derivative with the inner surface of the glass tube has brought about many advantages, such as preventing of scaling-off or exfoliation of the layer of stationary phase even in a high-speed separation, elimination of necessary pre-saturation of mobile phase with the stationary phase, elimination of a pre-column, free selection of mobile phase composition, preventing of column efficiency deterioration and variation of retention time, and improvement of reproductivity of chromatogram. Further merits of this invention can be enumerated as (1) compacting the size of chromatograph due to miniaturising of the column through the minimizing of the inner diameter thereof, and (2) improvement of sensitivity and the resultant capability of super-microanalysis, because of decreasing the dilution of sample by the mobile phase, which is attributable to the decrease of flowing speed of the mobile phase down to approximately a few $\mu l/min.$ and of sample amount down to approximately decades of nl.

DETAILED DESCRIPTION OF PREFERRED EMBODIMENTS

Figure 1:
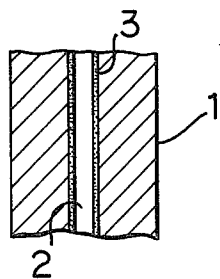
FIG. 1 is a vertical cross-sectional view, in part, of a column of a first embodiment in accordance with this invention.

An open tubular capillary column, made of glass material, of extremely small inner diameter to be used in this invention is easily obtainable by a usual glass tube extending or extruding machine for making the tubes used in gas chromatography. The inner diameter thereof is however required to be not more than 0.10 mm, and in actuality columns of the inner diameter 0.05–0.08 mm are manufactured. The length of columns must be determined such that the net inside capacity of the column may not be less than 0.5 $\mu l$, preferably not less than 1.0 $\mu l$. Columns outside of the above-mentioned conditions are of little use for the high-speed micro liquid chromatography, because they are low in the column separation efficiency, unadaptable for high-speed separation, and further problematical in sample injection and in detection of the separated components.

Such glass columns are desired, before being provided with a chemically bonded layer of silane or its derivative in accordance with this invention or the inner surface thereof, to be washed or rinsed clean. The cleaning can thereby advantageously impart lesser HETP (height equivalent to a theoretical plate) to the column; it will be further effective, if acid cleaning such as with hydrochloric acid and/or alkali cleaning such as with sodium hydroxide is executed, in addition to the usual water washing and/or methanol washing.

On the inner surface of such a column is chemically combined or bonded at least one silane or its derivative (hereinafter called silanizing agent), capable of becoming a stationary phase, with the base material of the glass tube, to form a polymeric layer of the silanizing agent there. Such a chemical bonding or combination, an action between theinner surface of the glass tube and the silanizing agent, is thought to be attributable to the chemical reaction of the silanizing agent to the silanol groups

existing in the base material of the glass tube inside surface. When tri-substituted-chlorosilane (R′ R″ R‴ Si Cl) is used as a silanizing agent, such a chemical reaction as stated below is thought to take place,

This reaction can be assumed to be valid when the silanizing agent is monoactive or monofunctional, and monolayer of stationary phase is consequently formed. When the silanizing agent is polyfunctional, having two or three reactive groups (in case the sum m+n being 2 or 1), the chemical reaction there will be far more complicated; a stationary phase having a siloxane (Si—O) bond of two-dimensional or three-dimensional structure is formed on the inner surface of the glass tube. In this invention such stationary phases of poly-dimensional structure are recommended to be formed. As the silanizing agent capable of forming a stationary phase, substituted-halogenized silane, substituted-oxy silane, substituted siloxane, substituted silazane, substituted silanol, etc, can be enumerated. It is to be selected properly according to the object of use of the column, the sample used for separation, the kind of the mobile phase liquid used, etc. Such organic compounds which can be designated by the following rational formula are preferably employed,

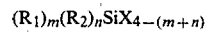

wherein $R_1$ and $R_2$ are respectively organic residual group acting as a stationary phase, which may be for example alkyl group, alkenyl group, aryl group, alalkyl group, alkylaryl group, and halogen or polar group (cyano group, amino group, etc.) substitution derivatives of the above-mentioned groups, and besides $R_1$ and $R_2$ further may be a combined ring, and may be in a same group or in a different group. Besides, x may be any one group or atom which can react with the OH in the silanol group existing in the inner surface of the glass column, for example, halogen atoms such as chlorine, bromine, etc., alkoxyl group, carboxyl group, phenoxy group, siloxy group, or halogenized derivatives of these groups, or others. In general, it is most preferable to be a kind of halogen. And m and n are respectively an integer in the range of 0–3, inclusive; the sum of m and n shall fall in the range of 1–3, inclusive. In this invention the sum of m and n shall most preferably be 1 or 2. As compounds which can be designated by these rational formula, under-mentioned substances are exemplarily enumerated methyltrichlorosilane, dimethyldichlorosilane, cyanoethyltrichlorosilane, trihexylbromosilane, octadecyltrichlorosilane, methyoctadecyltrichlorosilane, phenyltrichlorosilane, diphenyldichlorosilane, methyltriethoxysilane, p-tolyltrimethoxysilane, N-(2-aminoethyl)-γ-aminopropyltrimethoxysilane, etc. Any of such silanizing agents can be, by a usual method, applied or stuck onto the inner surface of the glass column, for example, flowing or passing a solution of a silanizing agent in a state of plug flow, which is called a dynamic method, vaporising a solvent in the solution of a silanizing agent already filled in the glass column, or sticking the silanizing agent on the inner surface of the glass column by passing a vapor of the silanizing agent or of the solution thereof. The silanizing agent stuck or coated on the inner surface of the glass column in such a manner may be converted into a chemically stable layer, by means of heating, through the chemical reaction between the silanol group existing in the inner surface of the glass column and the silanizing agent thus applied thereon. The layer becomes a chemically combined stable silane or its derivatives. The silanol group in the inner surface of the glass column is thought to be mostly reacted with the silanizing agent. The unreacted residual silanizing agent, if any, is preferable to be further polymerized. The polymerization of the residual unreacted silanizing agent makes the same an additional stationary phase which will expedite the separation function. The polymerization is actually practiced by heating in the presence of water, specifically speaking, heating the unreacted silanizing agent in the glass column while passing through steam (aqueous vapor).

It is of course thinkable, before forming polymeric layer of such a silanizing agent on the inner surface of the glass column, to apply a coarsening treatment such as forming whiskers or jogs (unevenness). Although it is a desirable treatment in increasing capacity and improving theoretical plate number, and consequently in increasing sample amount, it can not be said suitable, rather should be avoided in this invention wherein an extremely thin or fine column is used, because of its raising the back pressure of the column.

An open tubular capillary column 1 obtained by the invented method is provided with, as shown in FIG. 1, an almost flat polymeric layer 3 of silane or its derivative which has been chemically combined or bonded with the component matter of the inner surface 2 of the column 1. This almost flat polymeric layer chemically combined shows the earlier stated excellent effects. Such a column is, at one end thereof, connected to a pumping system 4, and at the other end connected to a detector system 5 in an actual use. A sample of predetermined amount is introduced from a sample injecting mechanism (not shown) into the chromatography system, specifically into the column 1 together with the mobile phase which is delivered from the pumping system 4. There occurs separation and analysis through the detection in the detector system 5. In a chromatography system incorporating the invented column, the sample introduction method and apparatus therefor, disclosed by Muneo Saito et al, in the Application U.S. Ser. No. 829,296 with the date of Aug. 31, 1977, is preferably employed for the sample introduction and the mobile phase supplying.

This invention will further be numerically or dimensionally described in detail according to the preferred embodiments.

FIRST EMBODIMENT

In an open tubular column of glass with the inner diameter 0.060 mm$\phi$ and the length 336 cm, 200 $\mu$l methanol, 100 $\mu$l 6 N HCl, 200 $\mu$l water, 100 $\mu$l, 1 N NaOH, 200 $\mu$l water, 200 $\mu$l methanol, and 200 $\mu$l toluene were flowed, in the order, followed by heating up to 200° C. while passing $N_2$ gas therethrough and drying for an hour, as the cleaning (rinsing) operation.

As a process of applying or coating a silane solution on the thus cleaned inside of the glass column 1, 70 $\mu$l of a solution of octadecyltrichlorosilane 20% (V/V) in toluene was flowed through the column 1 in a plug state at a rate of 4.6 cm/sec. Then heating from 20° C. up to 130° C. at the temperature raising rate 2° C./min. was executed under the stream of $N_2$ gas, and it was maintained at the highest temperature for eight hours from the starting time. In order to polymerize the unreacted silane in the column 1, after the treatment of drying and heating, it was heated again from 20° C. up to 150° C. at the temperature raising rate of 4° C./min., while flowing $N_2$ gas which was saturated with steam, being kept afterwards overnight at that temperature. Then it was heated again at 200° C. under the stream of $N_2$ gas for two hours for finishing the drying.

Upon setting a column thus obtained in a liquid chromatograph, a high-speed separation was executed under the following conditions:

sample: methyl alcohol solution 0.036 $\mu$l, containing benzene 3.3%, naphthalene 0.35%, biphenyl 0.045%, fluorene 0.050%, anthracene 0.007%, and pyrene 0.088%, was injected.

mobile phase: gradient $$\text{MeOH/H}_2\text{O } 30/70 \xrightarrow{13.3 \ \mu l} 30/70 \xrightarrow{30 \ \mu l} 50/50$$

flow rate of a mobile phase: 2.22 $\mu$l/min.

detection system: ultraviolet spectrophotometer (detection wave length 254 nm)

Figure 3:
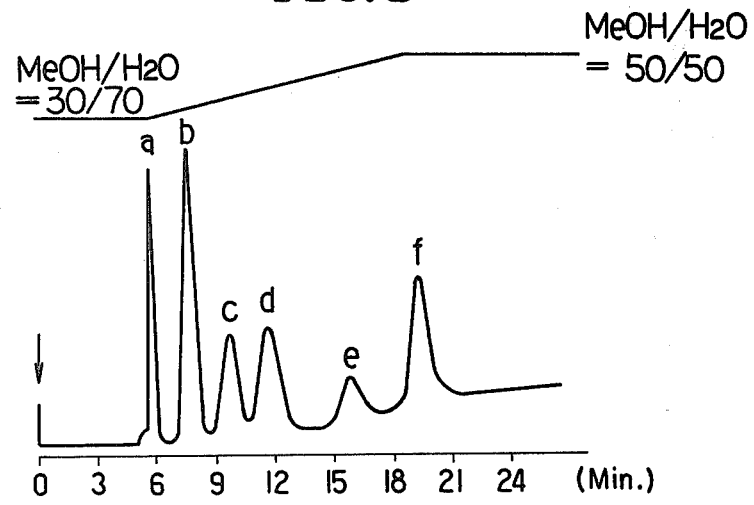
FIG. 3 is a chromatogram obtained in the first embodiment of this invention.

In this experiment, as shown in the chromatogram of FIG. 3, even that extremely small amount of sample proved the excellent separation, in which chromatogram symbols a to f respectively shows the peak of benzene, naphthalene, biphenyl, fluorene, anthracene, and pyrene.

SECOND EMBODIMENT

In an open tubular column of glass with the inner diameter 0.060 mm$\phi$ and the length 336 cm, 200 $\mu$l methanol, 100 $\mu$l 6N NCl, 200 $\mu$l water, 100 $\mu$l 1N NaOH, 200 $\mu$l water, 200 $\mu$l methanol, and 200 $\mu$l toluene, were flowed, in the order, followed by heating up to 200° C. while passing $N_2$ gas therethrough and drying for an hour, as the cleaning operation.

As the process of applying or coating a silane solution on the thus cleaned inside of the glass column 1, 70 $\mu$l of a solution of octadecyltrichlorosilane 20% (V/V) in toluene was flowed through the column 1 in a plug state at a rate of 4.6 cm/sec. The heating from 20° C. up to 130° C. at the temperature raising rate 2° C./min. was executed under the stream of $N_2$ gas, and it was maintained at the highest temperature for eight hours from the starting time. In order to polymerize the unreacted silane in the column 1, after the treatment of drying and heating, it was heated again from 20° C. up to 150° C. at the temperature raising rate of 4° C./min. while flowing $N_2$ gas, which was saturated with steam, being kept afterwards for fifteen hours at that temperature. Then it was heated again at 200° C. for thirty minutes under the stream of $N_2$ gas for finishing the drying.

Upon setting the second column thus obtained in a liquid chromatograph, a high-speed separation was executed under the following conditions:

sample- methyl alcohol solution 0.024 μl, containing benzene 1.12%, naphthalene 0.12%, and biphenyl 0.024% was injected.

mobile phase: MeOH/H$_2$O=52/48 flow rate of a mobile phase: 2.22 μl/min.

detection system: ultraviolet spectrophotometer (detection wave length 254 nm)

Figure 4:
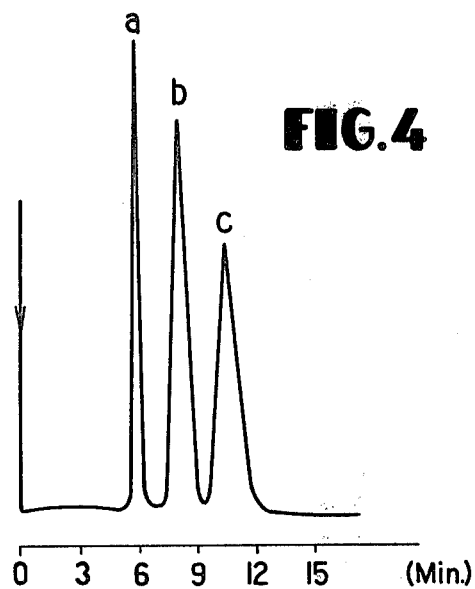
FIG. 4 is a chromatogram obtained in the second embodiment of this invention.
Figure 2:
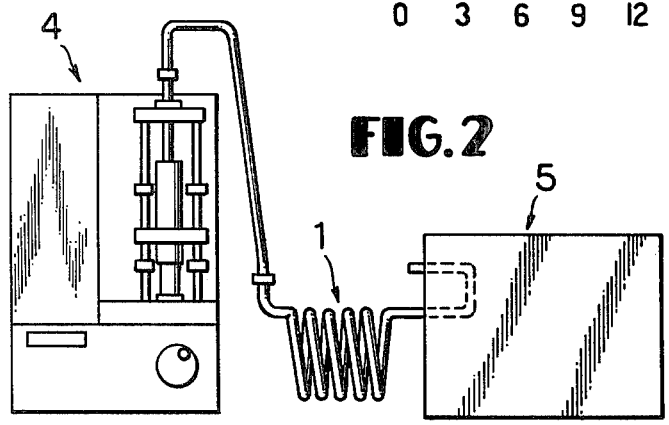
FIG. 2 is a schematic elevation of a liquid chromatograph in which a column of this invention is incorporated.

In this second experiment, as shown in the chromatogram of FIG. 4, even that very small amount of sample proved the excellent separation, in which chromatogram symbols a to c respectively shows the peak of benzene, naphthalene, and biphenyl.

These embodiments are disclosed herewith only for examples, and the invention should not be construed to be limited to the embodiments described. Variations and modifications are of course practicable for those skilled in the art without departing from the spirit and scope of this invention.

What is claimed is:

1. In a high-speed micro liquid chromatography apparatus comprising an open tubular capillary column made of glass tube, the improvement wherein the inner diameter of said glass tube is noyt more than 0.10 nm and the net inside capacity is not less than 0.5 μl, said glass tube being provided on the inner surface thereof with a stationary phase comprising a polymeric layer which is formed by a chemical bonding of at least one silane or its derivative with the inner surface of said glass tube.

2. An open tubular capillary column in accordance with claim 1, wherein said net inside capacity is not less than 1.0 μl.

3. An open tubular capillary column in accordance with claim 1, wherein the inner diameter of said glass tube is in the range between 0.05 mm and 0.08 mm.

4. An open tubular capillary column in accordance with claim 1, wherein said polymeric layer of silane or its derivative is produced by a chemical reaction between the silanol group on the inner surface of said glass tube and an organic compound which is represented by the following formula:

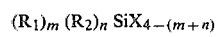

$$(R_1)_m (R_2)_n SiX_{4-(m+n)}$$

wherein $R_1$ and $R_2$ are respectively an organic residual group which acts as a stationary phase, X is a group or an atom which is reactive with a silanol group, m and n are respectively an integer in the range between 0 and 3, and the sum of m plus n is within the range of 1 to 3.

5. An open tubular capillary column in accordance with claim 4, wherein said organic compound is octadecyltrichlorosilane.

6. In an open tubular capillary column for high-speed micro liquid chromatography made of glass tubing and having a net inside capacity of not less than 1.0 μl, said glass tubing having a coating on its interior surface comprising a polymerized silane or derivative thereof, the improvement wherein the inner diameter of said glass tube is in the range of 0.05 mm to 0.08 mm.

* * * * *

UNITED STATES PATENT AND TRADEMARK OFFICE
CERTIFICATE OF CORRECTION

PATENT NO. : 4,207,188

DATED : June 10, 1980

INVENTOR(S) : TSUDA et al.

It is certified that error appears in the above-identified patent and that said Letters Patent are hereby corrected as shown below:

Claim 1, line 5, "noyt" should read --not--; "nm" should read --mm--

Signed and Sealed this

Seventeenth Day of February 1981

[SEAL]

Attest:

RENE D. TEGTMEYER

Attesting Officer

Acting Commissioner of Patents and Trademarks